United States Patent
Hedgpeth

(10) Patent No.: US 7,124,766 B1
(45) Date of Patent: Oct. 24, 2006

(54) APPARATUS AND USE THEREOF IN CLEANING A RESPIRATORY DEVICE

(76) Inventor: Rick L. Hedgpeth, 43 Lookout Trail, Fair Grove, MO (US) 65648

( * ) Notice: Subject to any disclaimer, the term of this patent is extended or adjusted under 35 U.S.C. 154(b) by 523 days.

(21) Appl. No.: 10/251,184

(22) Filed: Sep. 20, 2002

(51) Int. Cl.
  B08B 9/02 (2006.01)
  B08B 3/00 (2006.01)

(52) U.S. Cl. .............. 134/168 C; 134/169 C; 134/182; 134/184

(58) Field of Classification Search ........... 134/111, 134/168 C, 167 C, 169 C, 166 C, 182, 184, 134/195
See application file for complete search history.

(56) References Cited

U.S. PATENT DOCUMENTS

| | | | |
|---|---|---|---|
| 1,545,979 A | 7/1925 | Rosenberg | 134/104.4 |
| 2,675,012 A | 4/1954 | Scales | 134/85 |
| 3,033,712 A | 5/1962 | Brevik | 134/34 |
| 3,343,555 A | 9/1967 | Kasner | 134/111 |
| 3,522,814 A * | 8/1970 | Olson | 134/111 |
| 4,090,530 A | 5/1978 | Lange | 137/563 |
| 4,135,530 A | 1/1979 | Cheney | 134/60 |
| 4,261,378 A * | 4/1981 | Otzen | 134/56 R |
| 4,773,436 A | 9/1988 | Cantrell et al. | 134/108 |
| 5,014,737 A | 5/1991 | Berman | 137/334 |
| 5,203,367 A * | 4/1993 | Akai et al. | 137/101.25 |
| 5,246,025 A | 9/1993 | Cawlfield | 134/102.2 |
| 5,499,643 A * | 3/1996 | Vincent et al. | 134/104.4 |
| 5,720,308 A * | 2/1998 | Danowski et al. | 134/111 |
| 6,019,110 A * | 2/2000 | McClure et al. | 134/56 R |
| 6,044,854 A * | 4/2000 | Marks | 134/111 |
| 6,398,877 B1 * | 6/2002 | Magliocca | 134/10 |
| 6,432,215 B1 * | 8/2002 | Gamache et al. | 134/10 |

* cited by examiner

Primary Examiner—Joseph L. Perrin
(74) Attorney, Agent, or Firm—William R. Sharp

(57) ABSTRACT

A cleaning apparatus includes a tank housing and a partition disposed in the tank housing so as to divide the interior thereof into pumping and cleaning chambers as the only chambers within the tank housing adapted to contain cleaning liquid. A submersible pump mounted inside the pumping chamber has an outlet connected to a first end of at least one tubular member, which defines a flow path extending from the first end and through an opening in the partition to an opposing second end inside the cleaning chamber and connected to a respiratory device for cleaning thereof. Cleaning liquid is pumped from the pumping chamber along the flow path, through the device for interior cleaning, and into the cleaning chamber to fill such chamber to an upper end portion of the partition defining an overflow weir, thereby immersing ad the device for exterior cleaning and allowing overflow into the pumping chamber.

11 Claims, 1 Drawing Sheet

APPARATUS AND USE THEREOF IN CLEANING A RESPIRATORY DEVICE

BACKGROUND OF THE INVENTION

The invention relates to an apparatus and method for cleaning a respiratory device, particularly of the type comprising a mask and associated hose for conveying an oxygen-containing gas (i.e. air) to and through the mask.

Such a respiratory device is used with a CPAP (Continuous Positive Airway Pressure) machine in the treatment of obstructive sleep apnea. Obstructive sleep apnea is a condition that occurs when a person repeatedly stops breathing during sleep because his or her airway collapses and prevents air from reaching the lungs. The CPAP machine delivers air at a continuous pressure through a hose to a mask as worn by the patient over the nose and/or mouth. The resulting application of continuous air pressure inside the airway of the patient prevents the airway from collapsing and restores normal breathing during sleep.

The CPAP mask and associated hose must be cleaned regularly to minimize the presence of potentially pathogenic microorganisms. The CPAP mask, hose, and usually also a swivel adapter between the mask and hose are conventionally disassembled and then manually cleaned in a solution of water and mild detergent. Such a cleaning process is time consuming, inconvenient, and does not adequately clean interior surfaces. The cleaned components of the respiratory device must, of course, be reassembled after rinsing with water and drying.

SUMMARY OF THE INVENTION

Therefore, the object of the invention is to provide an apparatus and method of using the apparatus in cleaning a respiratory device that is convenient and effectively cleans interior as well as exterior surfaces.

According to one aspect of the invention, there is provided an apparatus comprising: a tank housing having an interior; a wall means disposed in the tank housing so as to divide the interior thereof into first and second chambers that are adapted to contain liquid therein, the wall means having an upper end portion which defines an overflow weir; a submersible pump inside the first chamber and having at least one inlet and an outlet, the inlet(s) being adapted to receive liquid from the first chamber; and a conduit means having opposing first and second ends between which a flow path is defined, the conduit means extending from the first end, to which the outlet of the pump is connected, and through the wall means to the second end inside the second chamber. Accordingly, liquid from the first chamber can be pumped by the submersible pump through the conduit means into the second chamber to fill the second chamber to the upper end portion of the wall means, thereby allowing overflow of liquid from the second chamber into the first chamber.

According to another aspect of the invention, there is provided a method of cleaning a respiratory device having an inlet end and an outlet end, wherein the method comprises: providing an apparatus which includes (i) a tank housing having an interior, (ii) a wall means having an upper end portion defining an overflow weir and being disposed in the tank housing so as to divide the interior thereof into a pumping chamber and a cleaning chamber, (iii) a submersible pump inside the pumping chamber and having at least one inlet and an outlet, and (iv) a conduit means having opposing first and second ends between which a flow path is defined, the conduit means extending from the first end, to which the outlet of the pump is connected, and through the wall means to the second end inside the cleaning chamber; placing the respiratory device in the cleaning chamber with said inlet end removably connected to the second end of the conduit means; providing a cleaning liquid in the pumping chamber and in the cleaning chamber; and operating the submersible pump so that cleaning liquid enters the inlet(s) of the pump from the pumping chamber and is expelled through the outlet of the pump so at flow through the conduit means, as extending through the wall means, and then through the respiratory device so as to exit the outlet end thereof into the cleaning chamber. The cleaning chamber is filled with cleaning liquid to the upper end portion of the wall means to thereby immerse the respiratory device in cleaning liquid and allow overflow of cleaning liquid into the pumping chamber, which is only partially filled with cleaning liquid.

Where the respiratory device is an assembly of components including a hose, mask, and swivel adapter, such components may remain assembled during cleaning with the inlet end of the hose being connected to the above-mentioned second end of the conduit means. The submersible pump can be operated for only several minutes to effectively clean the interior as well as exterior surfaces of the respiratory device. Flow of cleaning liquid through the components of the respiratory device clean their interior surfaces, and immersion of the respiratory device in the cleaning chamber and that circulation created by flow from the outlet end of the respiratory device (as defined by the mask) cleans the exterior surfaces. The cleaned respiratory device can be easily rinsed with water by simply draining the cleaning liquid from the pumping and cleaning chambers, replacing the thus drained cleaning liquid with water, and operating the submersible pump in the manner described previously. The invention requires no manual cleaning or disassembly and subsequent reassembly of the respiratory device to thereby save time and optimize convenience.

Furthermore, providing a submersible pump inside the pumping chamber, as well as a conduit means extending from the outlet of the pump and through the wall means into the cleaning chamber, is advantageous in requiring no elements of the above-described apparatus or associated connections outside of the chambers. This "self-contained" design further optimizes ease and convenience of use.

DETAILED DESCRIPTION OF A PREFERRED EMBODIMENT

Figure 1:
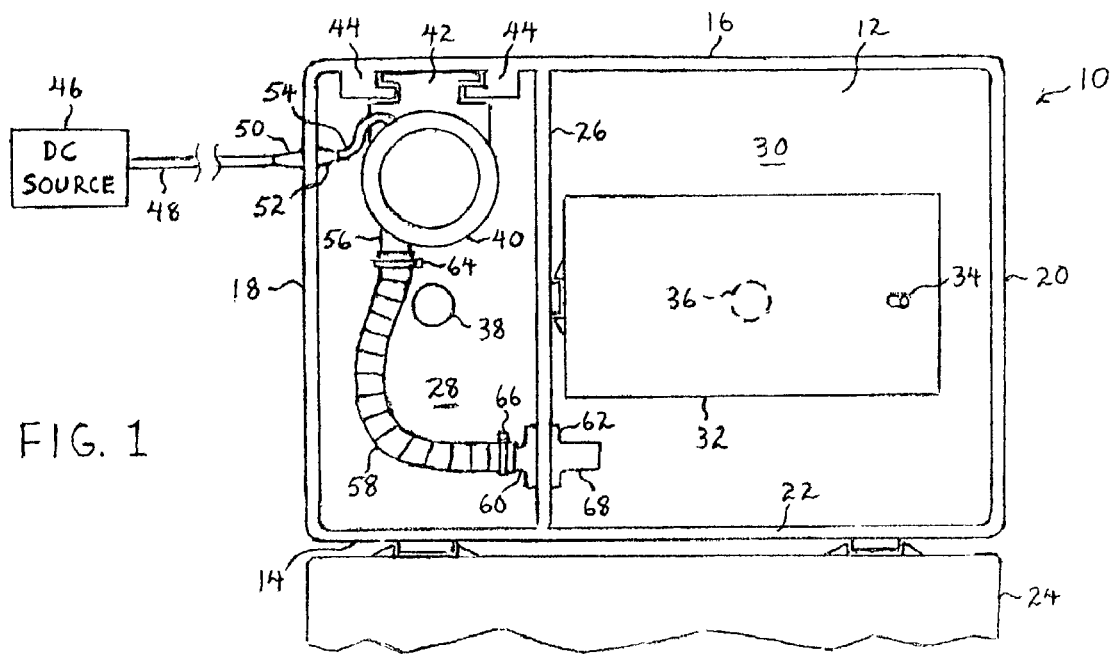
FIG. 1 is a top, plan view of an apparatus in accordance with the invention, showing a lid in an open position to reveal interior features.

Referring to FIG. 1, the illustrated apparatus includes a tank housing 10 having a bottom 12, opposing sides 14 and 16, opposing ends 18 and 20, and an open top 22. A lid 24 (only a portion being shown) is hingedly connected to side 14. As noted above, lid 24 is illustrated in an open position so that open top 22 is uncovered. Although not shown, lid 24 could have a sealing member around its peripheral edge to thereby seal against the upper edges of the sides and ends of tank housing 10 whenever the lid is closed.

A solid partition 26 (as the above-mentioned wall means) extends across the interior of tank housing 10 between sides 14 and 16 so as to divide such interior into a pumping chamber 28 and a cleaning chamber 30. Partition 26 is preferably connected between sides 14 and 16 so as to be integral therewith. A flap 32, as hingedly connected to an upper end portion of partition 26, has an upper face with a boss 34 projecting therefrom adjacent to that end of the flap opposite partition 26. AS shown, flap 32 has a width less than the width between sides 14 and 16. Hidden by flap 32, but indicated by a broken line, is a drain opening 36 through bottom 12 which communicates with cleaning chamber 30. A second drain opening 38 through bottom 12 is in communication with pumping chamber 28. Bottom 12 is closed except for drain openings 36 and 38.

A submersible pump 40 is fixedly but removably mounted inside pumping chamber 28. In the illustrated embodiment, pump 40 has an associated bracket 42 having a T-shaped end portion. A pair of ears 44, preferably integral with side 16, are shaped to securely but removably receive the T-shaped end portion therebetween as shown. Pump 40 is preferably electrically operated by a suitable DC source, as schematically indicated at 46. DC source 46 is most conveniently a commonly available AC/DC adapter that plugs into a 120V AC wall socket. An electrical cord 48 extends from DC source 46 to a plug 50 that is removably connected to jack 52 as mounted in end 18 of tank housing 10. An electrical cord 54 extends from jack 52 to pump 40. A switch (not shown) could be provided for the sake of convenience.

Submersible pump 40 can be, for example, a commercially available pump sold for use as a bilge pump by Attwood and other manufacturers. The pumping capacity of pump 40 is typically in the range of about 3–6 gallons per minute. Pump 40 has at least one inlet (shown and described subsequently with reference to FIG. 3) and an outlet 56.

A tubular conduit 58, preferably in the form of a flexible hose, has one end connected to outlet 56 and the other end connected to a portion 60 of a tubular connector 62. Tubular connector portion 60 extends from one side of partition 26 into pumping chamber 28. The respective ends of tubular conduit 58 are received over and removably secured to outlet 56 and tubular connector portion 60 with "zip" ties 64 and 66, or any other suitable fastening means. AS shown, tubular connector 62 has another portion 68 that extends from the other side of partition 26 into cleaning chamber 30.

Figure 2:
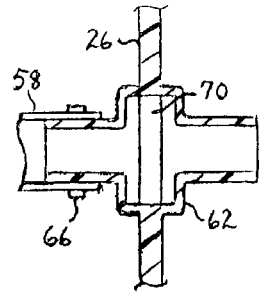
FIG. 2 is an enlarged, cross-sectional view of a tubular connector shown in FIG. 1.

Tubular conduit 58 and tubular connector 62 form a conduit means extending from that end of tubular conduit 58 connected to outlet 56, and through partition 26 to the end defined by tubular connector portion 68 inside cleaning chamber 30. A flow path is defined between such ends. Tubular conduit 58 defines a portion of the flow path, and tubular connector 62 defines the remainder of the flow path through an opening 70 extending between opposing sides of partition 26, as shown in FIG. 2. AS further shown in FIG. 2, tubular connector 62 is preferably integral with partition 26.

Figure 3:
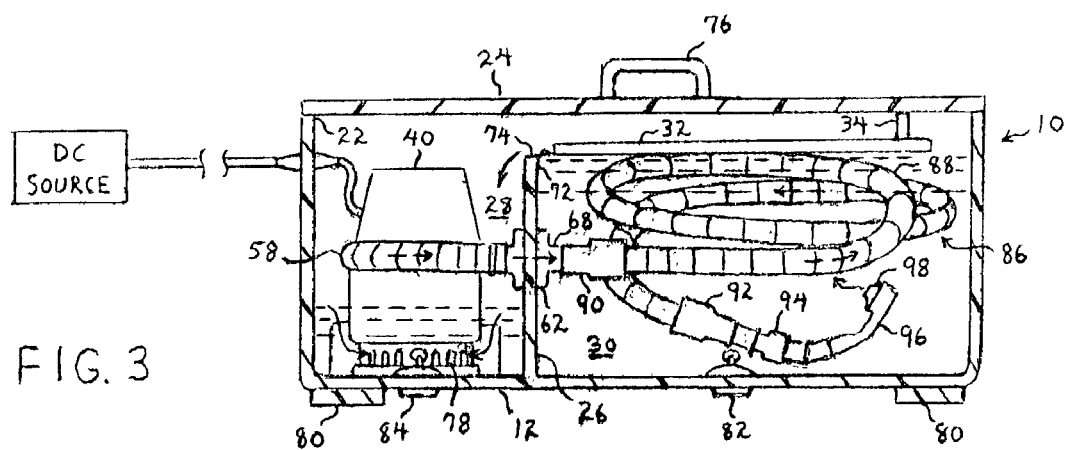
FIG. 3 is a cross-sectional view of the apparatus with its lid closed and having liquid therein in the course of operation.

Referring to FIG. 3, this cross-sectional view shows partition 26 vertically extending from bottom 12 of tank housing 10 to an upper end portion 72, which defines an upper edge 74 as an overflow weir adjacent to but below top 22. As an alternative not illustrated in the drawings, upper end portion 72 could define an overflow weir by having transversely spaced holes adjacent to upper edge 74. The term "overflow weir", as used herein and in the appended claims, refers to any structure over or through which excess liquid is allowed to flow.

As shown, flap 32 is hingedly connected to upper end portion 72 of partition 26 adjacent to upper edge 74. BOSS 34, as projecting from the upper face of flap 32, is engageable with lid 24 as received over open top 22 so that the lower face of flap 32 lies in a plane at the vertical level of upper edge 74 over cleaning chamber 30. Lid 24 preferably has a handle 76 for the convenience of the user.

Submersible pump 40 rests upon bottom 12 of tank housing 10 and has a plurality of inlet slots 78 adjacent to bottom 12. A leg 80 is affixed to or integral with each corner of bottom 12 to allow for drainage of liquid from tank housing 10, as will be discussed further below. Only two of four legs 80 are visible in the view of FIG. 3. Drain plugs 82 and 84 are sealingly and removably received in drain openings 36 and 38 (FIG. 1), respectively, while the apparatus is in use as shown.

Respiratory device 86, as received in cleaning chamber 30, is of the type used with a CPAP machine (not shown) and includes a tubular conduit 88 in the form of a flexible hose appropriately coiled in order to fit within the cleaning chamber. Tubular conduit 88 has opposing ends defined by flexible connectors 90 and 92. End connector 90 (having been previously removed from the outlet of the CPAP machine) is sealingly received over tubular connector portion 68 and its end (shown in FIGS. 1 and 2) so as to be removably connected thereto. End connector 90 functions as the inlet end of respiratory device 86. End connector 92 is sealingly and removably received over one end of a swivel adapter 94. The other end of swivel adapter 94 removably receives therein a tubular portion of a CPAP mask 96. The particular mask 96 shown in FIG. 3 is a nasal mask having a pair of nasal pillows 98 that define the outlet end of respiratory device 86. Only one of the nasal pillows is visible in FIG. 3. AS is known in the art, the nasal pillows are designed to fit into the nasal openings of the patient during sleep, and swivel adapter 94 allows rotation of mask 96 relative to tubular conduit 88. Associated headgear for holding the mask in position over the nose has been previously removed from mask 96.

It should be understood that although respiratory device 86 is illustrated with a particular type of nasal mask, the respiratory device could include any type of mask. The term "mask", as used herein and in the appended claims, refers to any respiratory accessory to be worn over the nose and/or mouth for delivering an oxygen-containing gas thereto.

Any suitable cleaning liquid can be used for cleaning respiratory device 86, such as a relatively diluted solution of water and a cleaning agent (i.e. mild detergent or vinegar). A predetermined volume of cleaning liquid is provided in pumping chamber 28 and cleaning chamber 30 so that the desired liquid levels as shown and discussed below are reached in the respective chambers during operation of submersible pump 40. AS indicated by the arrows, cleaning liquid enters the inlet slots 78 from pumping chamber 28 adjacent to bottom 12, and is expelled through outlet 56 (FIG. 1) so as flow into and through tubular conduit 58. The cleaning liquid continues to flow through tubular connector 62 and opening 70 (FIG. 2), and then through respiratory device 86 so as to exit the outlet end thereof (as defined by nasal pillows 98) into cleaning chamber 30. Cleaning chamber 30 is filled with cleaning liquid to upper end portion 72 and associated upper edge 74 to thereby immerse respiratory device 86 in cleaning liquid and allow cleaning liquid to flow over upper edge 74 into pumping chamber 28. As shown, pumping chamber 28 is only partially filled with cleaning liquid.

Interior surfaces of respiratory device 86 are thoroughly cleaned by the flow of cleaning liquid therethrough. Flap 32, in the position illustrated and previously described, ensures that the entire respiratory device 86 is immersed in cleaning liquid for optimum cleaning of exterior surfaces. Portions of respiratory device 86, particularly tubular conduit 88, will tend to float in the cleaning liquid. Flap 32 prevents any portion of respiratory device 86 from emerging above the upper level of the cleaning liquid in cleaning chamber 30. Respiratory device 86 is preferably positioned within cleaning chamber 30 so that mask 96 is approximately the lowermost portion of the device. Accordingly, this maximizes exposure of respiratory device 86 to the circulation of cleaning liquid within cleaning chamber 30, thereby further optimizing cleaning of exterior surfaces. Effective cleaning of respiratory device 86 is achieved by operating submersible pump 40 for only about 2–5 minutes.

After cleaning of the respiratory device with cleaning liquid in the manner described above with reference to FIG. 3, the pumping and cleaning chambers can be drained by removing the drain plugs from their respective drain openings. After placing the drain plugs back over the drain openings, the respiratory device can be rinsed by simply replacing the drained cleaning liquid with water and operating the submersible pump in the same manner discussed above to effectively rinse interior and exterior surfaces of the respiratory device. Once the water is drained from both chambers and the respiratory device is disconnected from the tubular connector and removed from the cleaning chamber, the respiratory device is allowed to dry and then reconnected to the CPAP machine.

With regard to preferred materials of construction for the illustrated apparatus, the tank housing, partition, and tubular connector, as well as the flap and lid, are preferably comprised of suitably moldable plastic. It is desirable but not necessary that the sides and ends of the tank housing are substantially transparent or translucent to permit the user to see inside the tank housing during operation in order to observe and monitor the contents thereof.

Obviously, many modifications and variations of the present invention are possible in light of the above teachings. For example, as an alternative to the hinged flap, a member or members could be affixed to the lid so as to define at least one surface lying in a plane at the vertical level of the partition upper edge when the lid is received over the open top of the tank housing. Or, a wall configured differently than the illustrated partition could define chambers of different shapes and relative orientations. It is, therefore, to be understood that the invention can be practiced otherwise than as specifically described.

That which is claimed is:

1. A cleaning apparatus for cleaning a respiratory device having a tubular inlet end and an outlet end, comprising:
    a tank housing having a bottom, opposing sides, a top, and an interior;
    a partition disposed in the tank housing so as to divide the interior thereof into first and second chambers that are adapted to contain cleaning liquid therein, the partition having an opening therethrough and an upper end portion which defines an upper edge as an overflow weir, adjacent to but below said top, over which cleaning liquid can flow, and wherein the partition vertically extends from said bottom to said upper end portion and also extends across the interior of the tank housing between said sides so as to divide said interior into the first and second chambers as the only chambers within the tank housing adapted to contain cleaning liquid;
    a submersible pump inside the first chamber and having at least one inlet and an outlet, said at least one inlet being adapted to receive cleaning liquid from the first chamber; and
    at least one tubular member having opposing first and second ends and defining a flow path extending from the first end, to which the outlet of the pump is connected, and through said opening to the second end positioned inside the second chamber so as to be adjacent to but spaced from the partition, thereby allowing the tubular inlet end of the respiratory device, when within the second chamber for cleaning, to be received over said second end and removably connected thereto, such that cleaning liquid from the first chamber can be pumped by the submersible pump along said flow path, into said tubular inlet end, and through the respiratory device so as to clean the interior thereof and exit its outlet end into the second chamber to fill such second chamber to the upper end portion and associated upper edge of the partition so as to exteriorly clean the respiratory device by immersion thereof in cleaning liquid, which overflows from the second chamber into the first chamber.

2. A cleaning apparatus as recited in claim 1 wherein the upper edge of the partition is at a vertical level in the tank housing and said top is open, said apparatus further comprising: a lid adapted to be removably received over the open top of the tank housing; and a surface defining means for defining, in conjunction with the lid as received over said open top, at least one surface lying in a plane at said vertical level over the second chamber.

3. A cleaning apparatus as recited in claim 2 wherein said surface defining means comprises a flap hingedly connected to said upper end portion adjacent to the upper edge thereof, the flap having a lower face, an upper face, and a boss projecting from said upper face and engageable with the lid as received over said open top so that said lower face defines said at least one surface lying in a plane at said vertical level, the flap also having a width less than the width between the sides of the tank housing.

4. A cleaning apparatus as recited in claim 3 wherein the bottom of the tank housing is closed except for first and second drain openings therethrough in communication with the first and second chambers, respectively, and wherein the apparatus further comprises first and second drain plugs adapted to be sealingly and removably received in the first and second drain openings, respectively.

5. A cleaning apparatus as recited in claim 1 wherein the submersible pump is fixedly mounted in the first chamber so as to rest upon the bottom of the tank housing.

6. A cleaning apparatus as recited in claim 5 wherein said at least one inlet of the submersible pump is adjacent to the bottom of the tank housing.

7. A cleaning apparatus as recited in claim 6 wherein the submersible pump is electrically operated.

8. A cleaning apparatus as recited in claim 1 wherein the overflow weir and said at least one tubular member as connected to the submersible pump provide the only communication between the first and second chambers.

9. A cleaning apparatus for cleaning a respiratory device having a tubular inlet end and an outlet end, comprising:
    a tank housing having a bottom, opposing sides, and an interior;

a partition disposed in the tank housing so as to divide the interior thereof into first and second chambers that are adapted to contain cleaning liquid therein, the partition having an opening therethrough, oppositely facing sides between which said opening extends, and an upper end portion which defines an overflow weir, and wherein the partition vertically extends from said bottom to said upper end portion and also extends across the interior of the tank housing between the sides thereof so as to divide said interior into the first and second chambers as the only chambers within the tank housing adapted to contain cleaning liquid;

a submersible pump inside the first chamber and having at least one inlet and an outlet, said at least one inlet being adapted to receive cleaning liquid from the first chamber;

a combination of tubular members having opposing first and second ends and defining a flow path extending from the first end, to which the outlet of the pump is connected, and through said opening to the second end positioned inside the second chamber so as to be adjacent to but spaced from the partition; and wherein said combination of tubular members comprises (i) a tubular conduit having opposing ends and defining a portion of the flow path therebetween, one end of the tubular conduit being said first end connected to the outlet of the pump, and (ii) a tubular connector defining the remainder of said flow path through said opening, the tubular connector having a first portion extending from one side of the partition into the first chamber and receiving thereover the other end of the tubular conduit so as to be connected thereto, the tubular connector further having a second portion extending from the other side of the partition into the second chamber and defining said second end, which as spaced from the partition allows the tubular inlet end of the respiratory device, when within the second chamber for cleaning, to be received over said second portion and second end defined thereby so as to be removably connected thereto, such that cleaning liquid from the first chamber can be pumped by the submersible pump along said flow path as defined by the tubular members, into said tubular inlet end, and through the respiratory device so as to clean the interior thereof and exit its outlet end into the second chamber to fill such second chamber to the upper end portion of the partition so as to exteriorly clean the respiratory device by immersion thereof in cleaning liquid, which overflows from the second chamber into the first chamber.

10. A cleaning apparatus as recited in claim 9 wherein the tank housing also has a top, and wherein said upper end portion defines an upper edge as the overflow weir, adjacent to but below said top, over which cleaning liquid can flow.

11. A cleaning apparatus as recited in claim 9 wherein the tubular conduit is a flexible hose.

\* \* \* \* \*